(12) United States Patent
Romiti et al.

(10) Patent No.: US 8,383,856 B2
(45) Date of Patent: Feb. 26, 2013

(54) PROCESS FOR UREA PRODUCTION AND RELATED PLANT

(75) Inventors: Domenico Romiti, Lugano (CH); Paolo Sticchi, Massagno (CH)

(73) Assignee: Urea Casale S.A. (CH)

( * ) Notice: Subject to any disclaimer, the term of this patent is extended or adjusted under 35 U.S.C. 154(b) by 364 days.

(21) Appl. No.: 11/817,186

(22) PCT Filed: Nov. 15, 2005

(86) PCT No.: PCT/EP2005/012252
§ 371 (c)(1),
(2), (4) Date: Apr. 24, 2008

(87) PCT Pub. No.: WO2006/094541
PCT Pub. Date: Sep. 14, 2006

(65) Prior Publication Data
US 2008/0219900 A1    Sep. 11, 2008

(30) Foreign Application Priority Data
Mar. 3, 2005  (EP) ..................................... 05004732

(51) Int. Cl.
*C07C 273/04* (2006.01)
*C07C 273/14* (2006.01)
*C07C 275/02* (2006.01)
*C01B 21/12* (2006.01)

(52) U.S. Cl. ................ 564/67; 423/365; 564/1; 564/32; 564/63; 564/66

(58) Field of Classification Search ................ 564/1, 32, 564/63, 67, 66; 423/365
See application file for complete search history.

(56) References Cited

U.S. PATENT DOCUMENTS

| | | | |
|---|---|---|---|
| 3,232,983 A | 2/1966 | Flinn | |
| 4,198,191 A * | 4/1980 | Pierce | ........................... 417/369 |
| 4,613,697 A * | 9/1986 | Pagani | ............................ 564/67 |
| 5,533,890 A * | 7/1996 | Holst et al. | ........................ 431/5 |
| 6,287,525 B1 | 9/2001 | Pagani | |
| 2002/0188157 A1* | 12/2002 | Fukunaka et al. | .............. 564/72 |
| 2005/0038293 A1 | 2/2005 | Jonckers et al. | |

FOREIGN PATENT DOCUMENTS

JP    08-325222    * 12/1996

* cited by examiner

*Primary Examiner* — Daniel C McCracken
*Assistant Examiner* — Daniel Berns
(74) *Attorney, Agent, or Firm* — Akerman Senterfitt

(57) ABSTRACT

A process for urea production from ammonia and carbon dioxide, made to react at a predetermined high pressure in an appropriate synthesis reactor (112), from the reaction between $NH_3$ and $CO_2$ being obtained a reaction mixture comprising urea, ammonium carbamate and free ammonia in aqueous solution, from which a recovery of ammonium carbamate and ammonia is carried out with their subsequent recycle to the synthesis reactor (112), said recovery from the reaction mixture taking place through operative steps of decomposition of the ammonium carbamate into $NH_3$ and $CO_2$ and of their stripping and a subsequent operative step of their recondensation into ammonium carbamate that is recycled to the synthesis reactor, the said reaction mixture obtained from the reaction between ammonia and carbon dioxide being pumped to the operative steps of decomposition and stripping.

1 Claim, 2 Drawing Sheets

US 8,383,856 B2

PROCESS FOR UREA PRODUCTION AND RELATED PLANT

FIELD OF APPLICATION

The present invention refers, in its most general aspect, to a process for urea production from ammonia and carbon dioxide, made to react at a predetermined high pressure in an appropriate synthesis reactor.

In particular, the invention refers to a process of the aforementioned type in which a reaction mixture comprising urea, ammonium carbamate and free ammonia in aqueous solution is obtained from the reaction between $NH_3$ and $CO_2$, from which a recovery of ammonium carbamate and ammonia is carried out with their subsequent recycle to the synthesis reactor.

More specifically the present invention concerns a process of the type considered, in which the aforementioned recovery from the reaction mixture takes place through operative steps of decomposition of the ammonium carbamate into $NH_3$ and $CO_2$ and of their stripping and a subsequent operative step of their recondensation (partial or total) into ammonium carbamate that is recycled to the synthesis reactor.

The invention also refers to a plant for carrying out the aforementioned process.

PRIOR ART

It is well known to produce urea with a process of the type specified above, in which the operative step of decomposition and stripping of the ammonium carbamate is carried out in an appropriate stripper, using, for example, a flow of $CO_2$ (using the so-called "carbon dioxide stripping technology") obtaining ammonia and carbon dioxide, and in which the ammonia and carbon dioxide, thus freed from the aqueous reaction mixture (to which the excess ammonia—i.e. unreacted ammonia, i.e. the so-called free ammonia dissolved in the urea solution—and the carbon dioxide used for the stripping are added), are sent to a condenser for the reformation of carbamate to be recycled to the synthesis reactor. In particular, it is said that the individual operating steps of:
urea synthesis from $NH_3$ and $CO_2$,
carbamate decomposition and stripping of $NH_3$ and $CO_2$,
their recondensation to carbamate and recycle to the synthesis reactor,
constitute a high pressure loop.

It is also known that, in accordance with the constant teaching of the prior art, the recycle flows that cross the synthesis reactor, the stripper and the condenser, are maintained solely by the pressure differences generated in the process itself. The particular arrangement and mutual correlation of the aforementioned apparatuses is designed so that the driving force of the flow through them is provided by variations of phase (and therefore of fluid density), determined in particular by the supply of heat in the stripper and by the removal of heat in the condenser.

In particular, given that the synthesis reactor and the condenser are positioned about 10 m above the stripper (vertical layout), the driving force resulting from the evaporation in the stripper and from the subsequent condensation in the condenser (and reactor) is of the order of 1 bar. This pressure difference is the result of the difference between the force of gravity acting upon the reaction mixture in the duct between synthesis reactor and stripper and the force of gravity exerted upon the gaseous flow of ammonia and carbon dioxide, in the duct between stripper and condenser.

This pressure difference of 1 bar is sufficient to counteract the pressure drop that occurs in the ducts and in the apparatuses themselves.

In these vertical layout conditions, it is said that the aforementioned high pressure loop is substantially isobar, since the aforementioned individual operating steps are carried out substantially at the same predetermined high pressure of the synthesis reactor. Moreover, it is said that the circulation of the flows between synthesis reactor, stripper and condenser is a natural circulation.

Although advantageous from different points of view, a process for urea production of the aforementioned type (stripping process), has recognized drawbacks due above all exactly to the obligatory arrangement (vertical layout) described above and that occur when one has to deal with the requirement of increasing the production capacity of the synthesis reactor and therefore of the entire process.

Indeed, it is practically impossible to increase the production capacity of the synthesis reactor without causing serious lacks of balance in the circulation of the flows between synthesis reactor, stripper and condenser, i.e., basically, any variation of the designed pressure drops deleteriously modifies the natural circulation provided in the entire substantially isobar loop. In other words, the aforementioned pressure difference of 1 bar is no longer sufficient to counteract the pressure drops due to the increase in capacity and therefore it is no longer possible to make the flow circulate again through the apparatuses of the high pressure loop.

Other drawbacks of the vertical layout of the aforementioned apparatuses are those linked to the construction costs of the raising that is necessary to the synthesis reactor and to the difficulties in maintaining the reactor itself raised with respect to the ground level. It should also be recalled that the construction of a reactor of large size (for example, 50-70 m in height), which operates at high pressure and which must be raised, requires the provision of complex and expensive safety structures like for example aseismic structures.

SUMMARY OF THE INVENTION

The technical problem forming the basis of the present invention is that of devising and providing a process for urea production of the so-called stripping process type considered above, and more specifically of providing the high pressure loop thereof, capable of overcoming the limitations and/or drawbacks quoted with reference to the prior art, in a simple and cost-effective manner.

This problem is solved, according to the present invention, by a process for urea production, comprising a high pressure loop of the type described above, characterized in that the said reaction mixture obtained from the reaction between ammonia and carbon dioxide is pumped to the operative steps of decomposition and stripping.

In this way it is possible, with great advantage, to rapidly vary the production capacity of a plant for the urea production by simply varying the parameters (pressure and/or flow rate) of a pump used for the aforementioned pumping to the operative steps of decomposition and stripping.

Moreover, in a plant that carries out the process of the invention, the synthesis reactor is allowed to be arranged at the same level as the stripper, i.e. a horizontal layout can be used.

In other words, in sharp contrast, with the constant teaching of the prior art that has created the technical prejudice of arranging the synthesis reactor raised with respect to the stripper to generate a pressure difference such as to create a natural circulation in the high pressure loop, the solution idea of the present invention is that of creating a pumping, i.e. a forced circulation, of the flow between synthesis reactor and stripper, varying the pumping parameters (pressure and/or flow rate) according to the desired production capacity of the plant.

Further characteristics and the advantages of the process for urea production according to the present invention shall become clear from the following description of a preferred embodiment thereof, made for indicating and not limiting purposes, with reference to the attached drawings.

DETAILED DESCRIPTION OF A PREFERRED EMBODIMENT

In order to simplify the description, only a portion of a plant for urea production that carries out the process of the present invention is shown schematically in the figures; more specifically, the high pressure urea synthesis section is shown, globally indicated with 110 (FIG. 1) and with 210 (FIG. 2), the remaining sections of the plant not being significant for the purposes of understanding the invention itself.

With reference to the aforementioned figures, the process for urea production according to the present invention comprises a first operative step in which ammonia and carbon dioxide are made to react at a predetermined high pressure in an appropriate synthesis reactor 112, obtaining a reaction mixture comprising urea, ammonium carbamate and free ammonia in aqueous solution.

From this aqueous solution, produced by the synthesis reaction and discharged by the synthesis reactor 112 substantially at the same high pressure at which said reaction is carried out, a recovery of ammonium carbamate and ammonia is carried out with their subsequent recycle to the synthesis reactor 112.

More specifically, said recovery from the reaction mixture takes place through operative steps of decomposition of the ammonium carbamate into $NH_3$ and $CO_2$ and of their stripping (in a stripper 114) and a subsequent operative step of their recondensation (partial or total) into ammonium carbamate (in a condenser 116).

In accordance with the present invention, the reaction mixture obtained from the reaction between ammonia and carbon dioxide is pumped to the operative steps of decomposition and of stripping.

Figure 1:
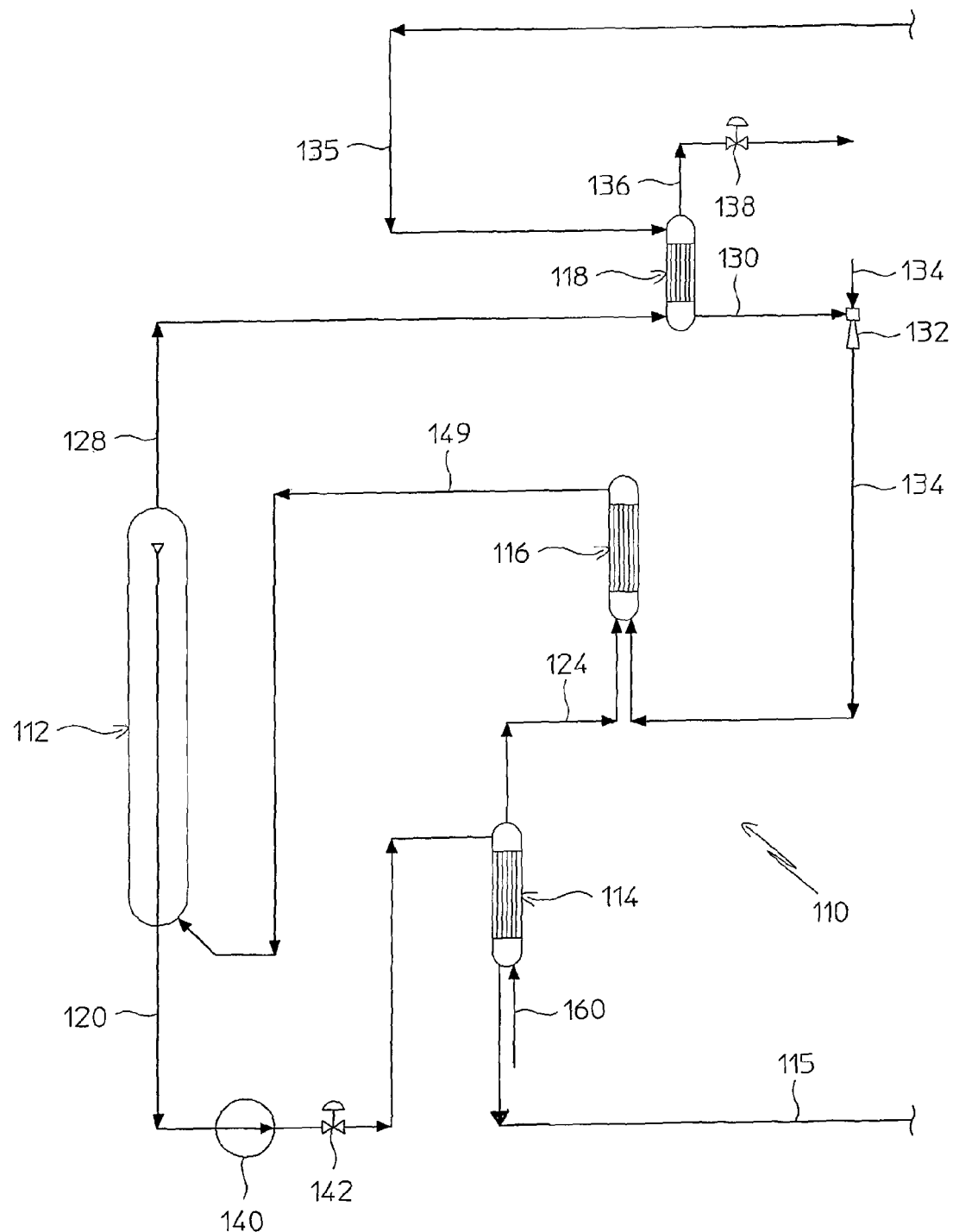
FIG. 1 schematically represents a high pressure urea synthesis section of a plant for urea production that carries out the process according to the invention.

In greater detail, FIG. 1 shows the high pressure urea synthesis section 110 of the plant for urea production that carries out the aforementioned process: it comprises the synthesis reactor 112, the stripper 114, the condenser 116 and a scrubber 118.

The reactor 112 and the stripper 114 are positioned with the respective bottoms substantially at the same height with respect to the ground and more specifically are put substantially on the ground level (for this reason, the synthesis section 110 is said to have a horizontal layout).

The condenser 116 is positioned with the lower bottom above the upper bottom of the stripper 114, for example 10 m above it.

In the example considered, the scrubber 118 is positioned with the lower bottom above the upper bottom of the reactor 112.

The reactor 112 is in fluid communication, through a duct 120, with the stripper 114.

In accordance with a characterizing aspect of the process of the present invention, a pump 140 is arranged on the duct 120. Alternatively, many pumps can be used, arranged in series or in parallel.

In accordance with a preferred embodiment of the present invention, downstream of the pump 140 the pressure on said reaction mixture is advantageously at least 1 bar greater than the pressure at which the urea synthesis reaction takes place in the reactor 112, or than the pressure upstream of the pump, so as to be greater than the operating pressure of the stripper 114 (so as to allow the inlet of said aqueous solution into the stripper 114 itself, the inlet of the vapours produced in said stripper 114 into the condenser 116 and the inlet of the carbamate produced in said condenser 116 into the synthesis reactor 112).

Preferably, the pump 140 is a canned rotor pump or a magnetic drive centrifugal pump.

On the duct 120, downstream of the pump 140, a control valve 142 is arranged. The stripper 114, as well as being in fluid communication, through a duct 124, with the condenser 116, is in fluid communication, through a duct 115, with a urea recovery section (per se conventional and for this reason not illustrated in figure) of the plant for urea production. Carbon dioxide ($CO_2$) is also fed to the stripper 114 through duct 160.

The condenser 116 is in fluid communication, through a duct 149, with the reactor 112.

The scrubber 118 is in fluid communication, through a duct 128, with the reactor 112.

The scrubber 118 is also in fluid communication, through a duct 130, with an ejector 132. The ejector 132 is arranged on a duct 134 that feeds ammonia to the condenser 116, ammonia being the driving fluid of the ejector 132. A diluted recycle carbamate solution coming from the urea recovery section is also returned to the scrubber 118, through a duct 135.

The scrubber 118 is furthermore in fluid communication, through a duct 136, with a vent, not illustrated in the figure. A control valve 138 is also provided on the duct 136.

The operation of the synthesis section 110 follows the process of the invention and is specified hereafter.

Ammonia and carbon dioxide are fed into the reactor 112 obtaining a reaction mixture comprising urea, ammonium carbamate and free ammonia in aqueous solution; the action of the pump 140 makes said reaction mixture flow to the stripper 114, through the duct 120.

In the stripper 114, said reaction mixture is subjected to decomposition of the carbamate into $NH_3$ and $CO_2$ and to their stripping using the feed carbon dioxide as stripping agent, obtaining a flow comprising ammonia and carbon dioxide in gaseous phase and a flow comprising urea and residual carbamate in aqueous solution; the duct 124 feeds said flow including ammonia and carbon dioxide in gaseous phase to the condenser 116, whereas said flow comprising urea and residual carbamate in aqueous solution is fed through the duct 115 to the urea recovery section, not illustrated in figure. In the condenser 116, said flow comprising ammonia and carbon dioxide in gaseous phase is subjected to condensation (partial or total), obtaining carbamate in aqueous solution; the duct 149 feeds said carbamate in aqueous solution to the reactor 112.

The duct 128 feeds a gaseous flow of inert gases, essentially including ammonia, carbon dioxide and steam, to the scrubber 118. In the scrubber 118, said gaseous flow is subjected to absorption through the diluted recycle carbamate solution coming from the duct 135.

The duct 130 feeds said recycle carbamate solution that has carried out the absorption of the flow of inert gases, to the ejector 132. The ejector 132 takes care of sending to the condenser 116, through the duct 134, both said recycle carbamate solution and ammonia fed into the duct 134 as driving fluid of the ejector.

Figure 2:
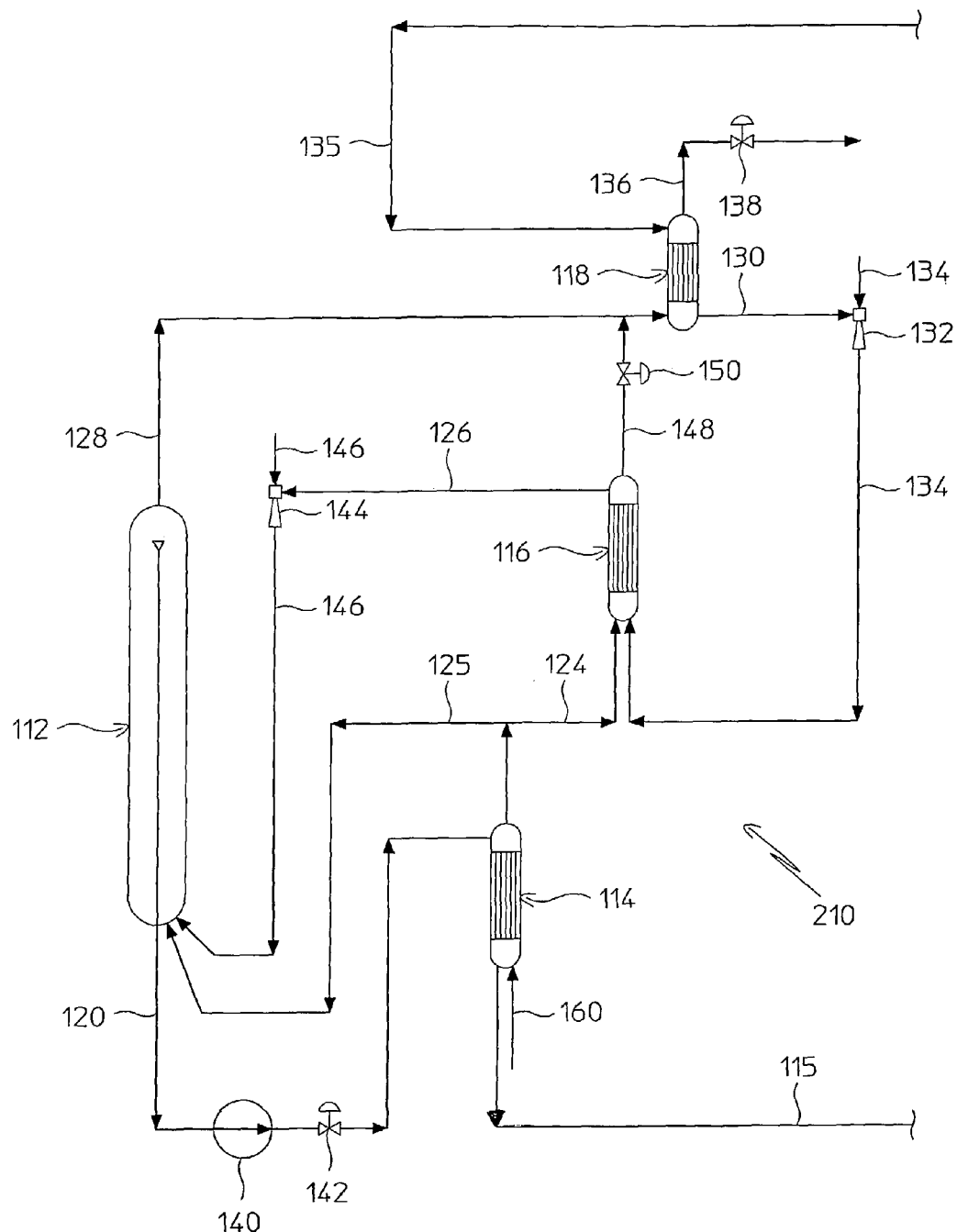
FIG. 2 schematically represents a high pressure urea synthesis section of a further plant for urea production that carries out the process according to the invention.

FIG. 2 shows the high pressure urea synthesis section 210 of a further plant for urea production that carries out the process according to the invention. In such a figure, the components structurally and/or functionally equivalent to those illustrated in FIG. 1 shall be indicated with the same reference numerals and shall not be described any further.

A duct 125 in fluid communication with the reactor 112 in inserted into the duct 124.

In place of the duct 149 a duct 126 is provided, which puts the condenser 116 in fluid communication with an ejector 144.

The ejector 144 is arranged on a duct 146 that feeds ammonia to the reactor 112, ammonia being the driving fluid of the ejector 144.

The condenser 116 is also in fluid communication, through a duct 148, with the duct 128. A control valve 150 is arranged on the duct 148.

The operation of the synthesis section 210 differs from that of the synthesis section 110 essentially in that the condenser 116 carries out a so-called total condensation, in a per se known way, unlike the condenser 116 of the synthesis section 110 that carries out a so-called partial condensation.

The duct 125 feeds a minority portion of the gaseous flow comprising ammonia and carbon dioxide from the stripper 114 directly to the synthesis reactor 112 for the urea synthesis, whereas the duct 124 feeds a majority portion of such a flow to the condenser 116.

The duct 126 feeds said carbamate in aqueous solution to the ejector 144. The ejector 144 takes care of sending to the reactor 112, through the duct 146, both said carbamate in aqueous solution and ammonia fed into the duct 146 as driving fluid of the ejector.

The duct 148 feeds a gaseous flow of inert gases to the duct 128.

It should be noted that it is very advantageous, in an existing plant for urea production, with a vertical layout of the synthesis reactor and of the stripper, to carry out a plant modernization that makes it carry out the process of the invention. In this way, keeping the existing layout of the synthesis reactor, of the stripper and of the condenser, it is possible to increase the design production capacity.

It should also be noted that, advantageously, both the canned rotor pump, and the magnetic drive centrifugal pump operate optimally in the required operating conditions (high flow rates and low discharge head, for example 1 or 2 bar) and ensure very high reliability.

From the previous description it can clearly be seen that the process for urea production according to the invention solves the technical problem and achieves numerous advantages the first of which lies in the fact that a horizontal layout of the synthesis section of the plant for urea production is allowed, which allows the investment and maintenance costs of the plant itself to be reduced, as well as considerably improving the safety conditions thereof.

Another great advantage of the invention is that of allowing a significant increase in the production capacity of an existing plant to be carried out, in particular it allows the productivity of the synthesis reactor to be developed without having to modify the layout of the plant itself.

Of course, a man skilled in the art can bring numerous modifications and variants to the process for urea production described above, in order to satisfy specific and contingent requirements, all of which are covered by the scope of protection of the present invention, as defined by the following claims.

What is claimed is:

1. A process for urea production from ammonia and carbon dioxide, comprising the steps of:

feeding ammonia and carbon dioxide to an appropriate synthesis reactor;

reacting said ammonia and carbon dioxide at a predetermined pressure in said appropriate synthesis reactor obtaining a reaction mixture comprising urea, ammonium carbamate and free ammonia in aqueous solution;

recovering ammonium carbamate and ammonia from said reaction mixture comprising urea, ammonium carbamate and free ammonia in aqueous solution through the operative steps of:

decomposing and stripping the ammonium carbamate into $NH_3$ and $CO_2$;

feeding a minority portion of a gaseous flow comprising $NH_3$ and $CO_2$ from the operative steps of decomposition and stripping directly to the synthesis reactor; and feeding a majority portion of said gaseous flow comprising $NH_3$ and $CO_2$ to a total recondensing step comprising recondensing said $NH_3$ and $CO_2$ in said majority portion into ammonium carbamate; and recycling said recovered ammonium carbamate and ammonia to said synthesis reactor, said steps of reacting, recovering and recycling belonging to a same pressure loop;

wherein said reaction mixture comprising urea, ammonium carbamate and free ammonia in aqueous solution obtained in said synthesis reactor is pumped to the operative steps of decomposition and stripping using at least one canned rotor pump.

\* \* \* \* \*